US006310241B1

(12) United States Patent
Karim et al.

(10) Patent No.: US 6,310,241 B1
(45) Date of Patent: Oct. 30, 2001

(54) CATALYSTS METHODS FOR PRODUCING ACETIC ACID FROM ETHANE OXIDATION USING MO, V, PD AND NB BASED CATALYSTS, PROCESSES OF MAKING SAME AND METHODS OF USING SAME

(75) Inventors: Khalid Karim, Burnage (GB); Edouard Mamedov, Houston, TX (US); Mohammed H. Al-Hazmi, Riyadh (SA); Anis H. Fakeeha, Riyadh (SA); Mustaf A. Soliman, Riyadh (SA); Yousef S. Al-Zeghayer, Riyadh (SA); Ahmed S. Al-Fatish, Riyadh (SA); Abdulsalm A. Al-Arify, Riyadh (SA)

(73) Assignee: Saudi Basic Industries Corporation (SA)

(*) Notice: Subject to any disclaimer, the term of this patent is extended or adjusted under 35 U.S.C. 154(b) by 0 days.

(21) Appl. No.: 09/461,086

(22) Filed: Dec. 14, 1999

Related U.S. Application Data

(62) Division of application No. 08/997,913, filed on Dec. 24, 1997, now Pat. No. 6,030,920.

(51) Int. Cl.[7] ................................................ C07C 51/215
(52) U.S. Cl. ........................................... 562/549; 562/607
(58) Field of Search ................................... 562/548, 607, 562/534, 535, 549

(56) References Cited

U.S. PATENT DOCUMENTS

| | | | |
|---|---|---|---|
| 3,057,915 | 10/1962 | Riemenschneider et al. | 260/533 |
| 3,240,805 | 3/1966 | Naglieri | 260/533 |
| 3,301,905 | 1/1967 | Riemenschneider et al. | 260/597 |
| 3,865,873 | * 2/1975 | Oda et al. . | |
| 4,148,757 | 4/1979 | Brazdil et al. | 252/432 |
| 4,250,346 | 2/1981 | Young et al. | 585/658 |
| 4,339,355 | 7/1982 | Decker et al. | 252/464 |
| 4,415,752 | * 11/1983 | Decker et al. . | |
| 4,524,236 | 6/1985 | McCain | 585/658 |
| 4,568,790 | 2/1986 | McCain | 585/658 |
| 4,596,787 | 6/1986 | Manyik et al. | 502/312 |
| 4,899,003 | 2/1990 | Manyik et al. | 585/313 |
| 5,153,162 | 10/1992 | Kurimoto et al. | 502/209 |
| 5,162,578 | 11/1992 | McCain, Jr. et al. | 562/512.2 |
| 5,300,682 | 4/1994 | Blum et al. | 562/512.2 |

FOREIGN PATENT DOCUMENTS

| | | | |
|---|---|---|---|
| 0 294 845 A | 12/1988 | (EP) | 88/50 |
| 0 407 091 | 1/1991 | (EP) . | |
| 0 480 594 | 4/1992 | (EP) . | |
| 0 518 548 | 12/1992 | (EP) . | |
| 0 620 205 A | 10/1994 | (EP) | 94/42 |
| 0 627 401 | 12/1994 | (EP) . | |
| 9805619 | * 7/1997 | (WO) . | |
| 05619 | * 2/1998 | (WO) . | |

OTHER PUBLICATIONS

E.M Thorsteinson et al. "The Oxidative Dehydrogenetion of Ethane . . . " *Journal of Catalysis* vol. 52, pp. 116–132 (1978).

* cited by examiner

*Primary Examiner*—Gary Geist
*Assistant Examiner*—Robert W. Deemie
(74) *Attorney, Agent, or Firm*—Kramer Levin Naftalis & Frankel LLP

(57) ABSTRACT

An oxide catalyst comprising the elements Mo, V, Nb and Pd. The novel catalytic system provides both higher selectivity and yield of acetic acid in the low temperature one step vapor phase direct oxidation of ethane with molecular oxygen containing gas without production of side products such as ethylene and CO. The feed gas is contacted with a catalyst containing Mo, V, Nb, Pd and O in the ratio a:b:c:d:x where a is 1 to 5; b is 0 to 0.5; c is 0.01 to 0.5; d is 0 0.2 and x is a number determined by the valence of the other elements in the catalyst.

21 Claims, 1 Drawing Sheet

CATALYSTS METHODS FOR PRODUCING ACETIC ACID FROM ETHANE OXIDATION USING MO, V, PD AND NB BASED CATALYSTS, PROCESSES OF MAKING SAME AND METHODS OF USING SAME

This application is a division of application Ser. No. 08/997,913, filed Dec. 24, 1997, now U.S. Pat. No. 6,030,920 which is incorporated herein by reference.

BACKGROUND OF THE INVENTION

1. Field of Invention

The invention relates to improved catalysts, methods of making the same and methods of using the same in a process for low temperature oxydehydrogenation of ethane to acetic acid without or having reduced production of ethylene and CO by-products in the product stream based on the composition of the catalyst. The invention also relates to a one step vapor phase catalytic process using the novel catalyst featuring increased ethane conversion and higher selectivity to acetic acid up to 80% at particular process conditions.

2. Description of Related Art

Several publications are referenced in this application. These references describe the state of the art to which this invention pertains, and are hereby incorporated by reference.

Utilization of lower alkane ($C_1$–$C_4$) as feed stock to produce added value petrochemicals is an industrially desired process. Lower alkanes are low cost and environmentally acceptable because of their low chemical reactivity. There are only few commercially available chemical catalytic processes which utilize lower alkane as a feed, such as butane to maleic anhydride.

Acetic acid is conventionally produced by methanol carbonylation using expensive rhodium catalysts in a liquid phase homogeneous reaction. This requires complicated procedures for recovery of the catalyst and isolation of products. More recently, acetic acid has been produced from an expensive raw material, ethylene, with the production of acetaldehyde as a by-product.

The use of molybdenum and vanadium-containing catalyst systems for low temperature oxydehydrogenation of ethane to ethylene was reported by E. M. Thorsteinson et. al., *Journal of Catalysts*, vol. 52, pp. 116–132 (1978). This paper discloses mixed oxide catalysts containing molybdenum and vanadium together with another transition metal oxide, such as Ti, Cr, Mn, Fe, Co, Ni, Nb, Ta, or Ce. The catalysts are active at temperatures as low as 200° C. for the oxydehydrogenation of ethane to ethylene. Some acetic acid is produced as a by-product.

Several U.S. Pat. Nos. (4,250,346, 4,524,236, 4,568,790, 4,596,787 and 4,899,003) have been granted on low temperature oxydehydrogenation of ethane to ethylene. U.S. Pat. No. 4,250,346 discloses the use of catalysts of the formula $Mo_hV_iNb_jA_k$ in which A is Ce, K, P, Ni, and/or U, h is 16, i is 1 to 8, j is 0.2 to 10, and k is 0.1 to 5. U.S. Pat. No. 4,454,236 is directed to the use of a calcined catalyst of the formula $Mo_aV_bNb_cSb_dX_e$.

The above cited patents make reference to other patents concerned with the production of ethylene from ethane by the oxydehydrogenation process and all make reference to the formation of acetic acid as a by-product.

U.S. Pat. Nos. 4,339,355 and 4,148,757 disclose oxide catalysts containing Mo, Nb, V and a fourth metal selected from Co, Cr, Fe, In, Mn or Y for the oxidation/ammoxidation of unsaturated aliphatic aldehyde to corresponding saturated aliphatic carboxylic acids.

European Patent Publication EP 02 94 845 discloses a process for the higher selective production of acetic acid by the oxidation of ethane with oxygen in contact with a mixture of catalysts consisting of (A) a catalyst for oxydehydrogenation of ethane to ethylene and (B) a catalyst for hydration/oxidation of ethylene. The ethane oxydehydrogenation catalyst is represented by the formula $Mo_xV_yZ_z$, wherein Z can be one or more of the metals Nb, Sb, Ta, Ca, Sr, Ti and W. The catalyst for hydration/oxidation is selected from a molecular sieve catalyst, a palladium-containing oxide catalyst, tungsten-phosphorus oxides, or a tin molybdenum containing oxide catalysts. European Patent Publication EP 02 94 845 employs a catalyst prepared by a physical mixture of two types of catalysts. This patent does not disclose the catalyst of the present invention, which is designed in such a way that it has both oxydehydrogenation and oxygenation properties on the same catalyst.

European Patent Publication EP 04 80 594 is directed to the use of an oxide catalyst composition comprising tungsten, vanadium, rhenium and at least one of the alkaline metals for the production of ethylene and acetic acid by oxidation of ethane with a molecular oxygen-containing gas. The replacement of tungsten in whole or part by molybdenum carried out in European Patent Publication EP 04 07 091 results in an increase in selectivity to acetic acid at the expense of the selectivity to ethylene.

European Patent Publication EP 05 18 548 is concerned with a process for the production of acetic acid by ethane oxidation in contact with a solid catalyst having an empirical formula $VP_aM_bO_x$, where M is one or more optional elements selected from Co, Cu, Re, Nb, W and many other elements, excluding molybdenum, a is 0.5 to 3, b is 0 to 0.1.

European Patent Publication EP 06 27 401 describes the use of a $V_aTi_bO_x$ catalyst for the oxidation of ethane to acetic acid. The catalyst composition may comprise additional components from a large list of possible elements. The reference does not disclose any examples of catalysts comprising those elements in combination with vanadium, titanium and oxygen. Further, recently reported catalysts containing MoVNb promoted with phosphorus can produce a relatively higher yield of acetic acid as compared to unpromoted catalyst with the production of by products such as carbon monoxide, carbon dioxide and ethylene (U.S. application Ser. No. 08/932,075 (Attorney Docket No. 582815-2060), filed Sep. 17, 1997, entitled "Catalysts for the Oxidation of Ethane to Acetic Acid, Processes of Making Same and Processes of Using the Same", hereby incorporated by reference). Further, due to environmental law constraints, carbon monoxide is a less desirable by-product.

Accordingly, it would be desirable to produce an improved catalyst for use in the selective production of acetic acid from ethane through a single stage partial oxidation process without the production of carbon monoxide and ethylene.

SUMMARY OF THE INVENTION

According to the present invention, ethane is oxidized with molecular oxygen to acetic acid in a gas phase reaction at relatively high levels of conversion, selectivity and productivity and at temperatures ranging from 150° C. to 450° C. and at pressures ranging from 1–50 bar. This is achieved using a catalyst having a calcined composition of $Mo_aV_bNb_cPd_d$, wherein:

a is 1 to 5;

b is 0 to 0.5;

c is 0.01 to 0.5; and d is 0 to 0.2.

The numerical values of a, b, c and d represent the relative gram-atom ratios of the elements Mo, V, Nb and Pd, respectively, in the catalyst. The elements are present in combination with oxygen in the form of various oxides. The inventive catalysts are preferably produced using the methods disclosed herein.

BRIEF DESCRIPTION OF THE DRAWINGS

Specific embodiments of the present invention will now be described further, by way of example, with reference to the accompanying drawings, in which.

DESCRIPTION OF THE PREFERRED EMBODIMENTS

Figure 1:
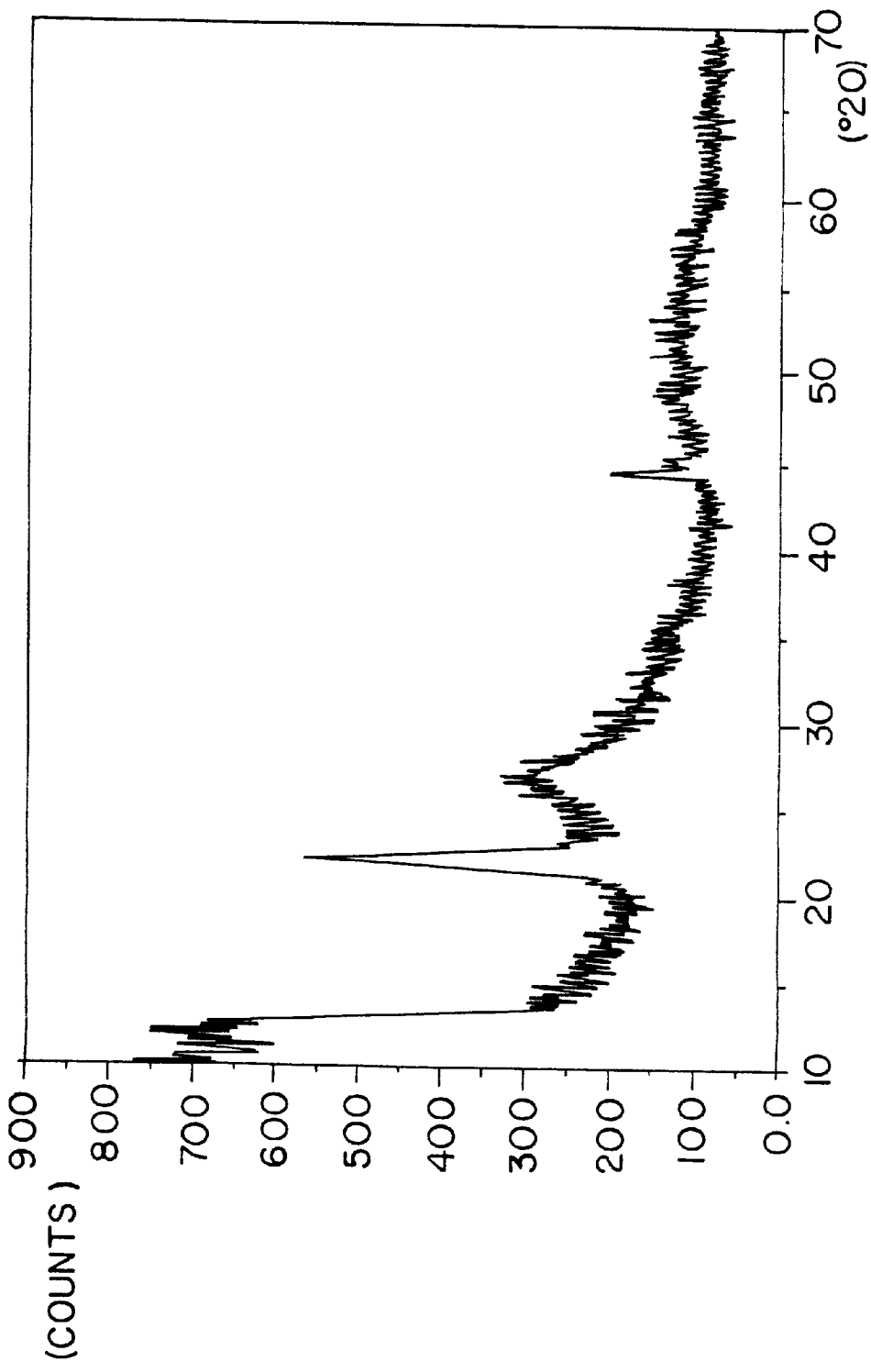
FIG. 1 is a graphical representation of an X-ray diffraction (XRD) pattern of a catalyst according to one embodiment of the invention.

The catalyst is a mixture of the elements in combination with oxygen. The catalyst can also be represented by the formula $Mo_{1-5} V_{0-0.5} Nb_{0.01-0.5} Pd_{0-0.2}O_y$, where y is a number determined by the valence requirements of the other elements in the catalyst composition.

The catalyst of the invention can be used with or without a support. Suitable supports for the catalyst include alumina, silica, titania, zirconia, zeolites, molecular sieves and other micro/nanoporous materials, and mixtures thereof. When used on a support, the supported catalyst usually comprises from about 10 to 50% by weight of the catalyst composition, with the remainder being the support material.

The choice of the compounds used as well as the specific procedures followed in preparing a catalyst can have a significant effect on the performance of a catalyst. It is believed the elements of the catalyst composition are in combination with oxygen as oxides.

Preferably, the catalyst is prepared from a solution of soluble compounds (salts, complexes or other compounds) of each of the metals. The solution is preferably an aqueous system having a pH of 1 to 10 and more preferably at a pH of 1 to 7, at a temperature of from about 30° C. to about 100° C.

Generally, a mixture of compounds containing the elements is prepared by dissolving sufficient quantities of soluble compounds and dispersing the insoluble compounds so as to provide a desired gram-atom ratios of the elements in the catalyst composition. The catalyst composition is then prepared by removing the water and/or other solvent from the mixture of the compounds in the solution system. The dried catalyst is calcined by heating to a temperature from about 250° C. to about 450° C. in air or oxygen for a period of time from about one hour to about 16 hours to produce the desired catalyst composition. Generally, the higher the temperature the shorter the period of time required.

Preferably, the molybdenum is introduced into the solution in the form of ammonium salts such as ammonium paramolybdate, or organic acid salts of molybdenum such as acetates, oxalates, mandelates, and glycolates. Some other partially water soluble molybdenum compounds which may be used include molybdenum oxides, molybdic acid, and chlorides of molybdenum.

Preferably, the vanadium is introduced into the solution in the form of ammonium salts such as ammonium metavanadate and ammonium decavanadate, or organic salts of vanadium such as acetates, oxalates, and tartrates. Partially water soluble vanadium compounds such as vanadium oxides, and sulfates of vanadium can be used. To achieve a complete solubility, a certain amount of oxalic or tartaric acid can be added.

The niobium is preferably used in the form of oxalates or hydrate oxide. Surprisingly, it has been discovered that niobium hydrate oxide is a preferred niobium precursor because it provides significant cost advantages by way of improved niobium yields in the resultant catalyst. According to one preferred embodiment of the invention, niobium hydrate is dissolved in oxalic acid at a temperature of about 85–99° C., preferably 90–95° C. Preferably, the niobium hydrate oxide:oxalic acid ratio is about 1:5. Other sources of this metal in soluble form include compounds in which the metal is coordinated, bonded or complexed to a beta-diketonate, carboxylic acid, and amine, and alcohol, or an alkanolamine.

Preferably, the palladium is introduced into the catalyst slurry in the form of Pd on activated charcoal or alumina or solution of salts of palladium such as acetate, chloride, etc.

Preferably, the catalyst is prepared by the following general procedure. Aqueous solution of vanadium, niobium and molybdenum are prepared separately. The vanadium solution is mixed with niobium solution at particular temperature and pH. The molybdenum solution is added to a VNb solution to form a combined gel. The fourth component, palladium, is slowly added to the combined gel solution. After mixing and heating for about ½ to 2 hours, the resultant gel is dried to incipient wetness with continuous stirring at about 100° C.

After drying the resultant gel mixture at 120° C. for 16 hours, the catalyst is heated to 350° C. at the rate of 2° per minute and calcined at this temperature in air for 4 hours to produce the desired oxide composition. This regime seems to be close to optimum as it allows to obtain a catalyst with the desired structure.

The catalysts disclosed in present invention preferably have a structure which is diffused or poorly crystallized patterns and can be characterized by the X-ray diffraction (XRD) pattern presented in Table 1 and FIG. 1.

TABLE 1

| Catalyst XRD characteristics | |
|---|---|
| Interplanar distance (Å) | Intensity |
| 4.00 | strong |
| 3.57 | diffused medium broad |
| 2.01 | weak |
| 1.86 | weak |

A strong reflection at 4.00 Å corresponds to orthorhombic and/or hexagonal $MoO_3$ phases (Ponselle, L., Wrobel, G., and Germain, J. E., *J. Microsc.*, vol. 7, page 949 (1968)). However, Thorsteinson et. al. has attributed this peak to Mo-vanadium containing phases in MoVNb catalytic system. Generally to obtain this structure, a catalyst has to be prepared by calcining at 350° C. by method described above. The broad peak at 3.57 is a kind of diffused peak and is difficult to attribute to any one phase especially when sample is calcined at a temperature of 350° C. During calcination at 350° C., the partially crystallized phase specified above is formed which is the active structure in the selective oxidation of ethane to acetic acid. Both amorphous or well-crystalline phases obtained by calcination at temperatures lower than 330° C. and higher than 370° C. are less effective with respect to production of acetic acid. Further, catalyst disclosed in the present invention does not show any additional peaks correspond to Pd containing material, FIG. 1.

Another aspect of the invention relates to the production of acetic acid from ethane without the production or with significantly reduced production of the by-products ethylene and CO in the product stream.

According to one embodiment of the invention, acetic acid is produced directly from ethane on a single step vapor phase catalytic process using the catalyst according to the invention.

The raw material used as the source for the ethane can be a gas stream which contains at least five volume percent of ethane. The gas stream can also contain minor amounts of the $C_3$–$C_4$ alkanes and alkenes, less than five volume percent of each. The gas stream can also contain major amounts, more than five volume percent, of nitrogen, carbon dioxide, and water in the form of steam.

The reaction mixture useful in carrying out the process is generally one mole of ethane, 0.01 to 2.0 moles of molecular oxygen either as pure oxygen or in the form of air, and zero to 4.0 moles of water in the form of steam. The water vapor or steam is used as a reaction diluent and as a heat moderator for the reaction and it also acts as a desorption accelerator of the reaction product in the vapor phase oxidation reaction. Other gases may be used as reaction diluents or heat moderators such as helium, nitrogen, and carbon dioxide.

The gaseous components of the reaction mixture include ethane, oxygen and a diluent, and these components are uniformly admixed prior to being introduced into the reaction zone. The components may be preheated, individually or after being admixed, prior to being introduced into the reaction zone.

The reaction zone generally has a pressure of from 1 to 50 bar, preferably from 1 to 30 bar; a temperature of from about 150° C. to about 450° C., preferably from 200° C. to 300° C.; a contact time between the reaction mixture and the catalyst of from about 0.01 second to 100 seconds, preferably from 0.1 second to 10 seconds; and a space hourly velocity of from about 50 to about 50,000 $h^{-1}$, preferably from 100 to 10,000 $h^{-1}$ and most preferably from 200 to 3,000 $h^{-1}$.

The contact time is defined as the ratio between the apparent volume of the catalyst bed and the volume of the gaseous reaction mixture feed to the catalyst bed under the given reaction conditions in a unit of time.

The space velocity is calculated by determining total reactor outlet gas equivalent in liters of the total effluent evolved over a period of one hour divided by the liters of catalyst in the reactor. This room temperature volume is converted to the volume at 0° C. at 1 bar.

The reaction pressure is initially provided by the feed of the gaseous reactant and diluent and after the reaction has commenced, is maintained by the use of a suitable back-pressure controller placed on the reactor outlet stream.

The reaction temperature is provided by placing the catalyst bed within a tubular converter having walls placed in a furnace heated to the desired reaction temperature.

The oxygen concentration in the feed gas mixture can vary widely, from 0.1 to 50% or higher of the feed mixture by applying of proper measures to avoid explosion problems. Air is the preferred source of oxygen in the feed. The amount of oxygen present may be a stoichiometric amount, or lower, of the hydrocarbons in the feed.

According to one preferred embodiment, the process is carried out in a single stage with all the oxygen and reactants being supplied as a single feed with unreacted initial reactants being recycled. However, multiple stage addition of oxygen to the reactor with an intermediate hydrocarbon feed can also be used. This may improve productivity to acetic acid and avoid a potentially hazardous condition.

The catalyst of the invention is not limited to the oxydehydrogenation of ethane to ethylene and acetic acid and may be used for oxidizing alpha-beta unsaturated aliphatic aldehydes in the vapor phase with molecular oxygen to produce the corresponding alpha-beta unsaturated carboxylic acids. Further, the catalyst of the invention can also be applied for oxidation of ethylene to acetic acid.

Accordingly, another aspect of the invention relates to a process for performing a catalytic chemical reaction comprising the step of introducing one or more reactants into a reaction zone containing the novel catalyst composition, wherein the catalytic chemical reaction preferably converts one or more fluid phase reactants to one or more fluid phase products. According to one preferred embodiment, the process oxidizes lower alkenes to produce the corresponding acids (e.g., ethane to acetic acid, propane to propionic acid, methane to formic acid and butane to butyric acid).

EXAMPLES

The following examples are illustrative of some of the products and methods of making the same falling within the scope of the present invention. They are, of course, not to be considered in any way limitative of the invention. Numerous changes and modification can be made with respect to the invention.

Catalyst Testing

Catalysts evaluation were carried out in a stainless steel fixed bed tubular reactor under standard process conditions. For the ethane-air system, the gas feed composition was 15% by volume ethane and 85% by volume air at a reaction temperature of 260° C., a pressure of 200 psig and at space velocity of about 1,100 $h^{-1}$ by using 3 g of calcined catalyst. For the enriched ethane system (ethane/oxygen), the gas feed composition was 82% by volume ethane (enriched hydrocarbon) and 18% by volume oxygen at a reaction temperature of 250° C., a pressure of 200 psig and at space velocity of about 5,000 $h^{-1}$ by using of 0.3 g of calcined catalyst.

Reaction products were analyzed on-line by gas chromatography. Oxygen, nitrogen and carbon monoxide were analyzed using a 2.5 m by 3 mm column of 13×molecular sieve. Carbon dioxide, ethane and ethylene were analyzed using a 0.5 m by 3 mm column packed with material sold under the trade name PORAPACK™ N. Acetic acid and water were analyzed using a 1.5 m by 3 mm column packed with material sold under the trademark HAYASEP™ Q. In all cases, the conversion and selectivity calculations were based on the stoichiometry:

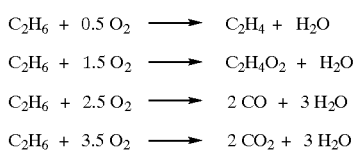

$$C_2H_6 + 0.5\,O_2 \longrightarrow C_2H_4 + H_2O$$
$$C_2H_6 + 1.5\,O_2 \longrightarrow C_2H_4O_2 + H_2O$$
$$C_2H_6 + 2.5\,O_2 \longrightarrow 2\,CO + 3\,H_2O$$
$$C_2H_6 + 3.5\,O_2 \longrightarrow 2\,CO_2 + 3\,H_2O$$

The yield of acetic acid was calculated by multiplying the selectivity to acetic acid by ethane conversion.

Three procedures for catalyst preparation were applied for the examples given in Table 1.

Group A: Examples 1, 2, 3, 4, 6, 7, 8, 9 and 12.
Group B: Examples 5, 10, 11, 13, 15 and 16.
Group C: Examples 14, 17, 18 and 19.

TABLE 2

Catalyst Compositions

| Example No. | CATALYST COMPOSITION |
| --- | --- |
| 1 | $Mo_1V_{0.396}Nb_{0.128}$ |
| 2 | $Mo_1V_{0.396}Nb_{0.128}Pd_{4.99E-05}$ |
| 3 | $Mo_1V_{0.396}Nb_{0.128}Pd_{9.60E-05}$ |
| 4 | $Mo_1V_{0.396}Nb_{0.128}Pd_{1.44E-04}$ |
| 5 | $Mo_1V_{0.396}Nb_{0.128}Pd_{1.90E-04}$ |
| 6 | $Mo_1V_{0.396}Nb_{0.128}Pd_{1.92E-04}$ |
| 7 | $Mo_1V_{0.396}Nb_{0.128}Pd_{1.92E-04}$ |
| 8 | $Mo_1V_{0.396}Nb_{0.128}Pd_{1.92E-04}$ |
| 9 | $Mo_1V_{0.396}Nb_{0.128}Pd_{1.92E-04}$ |
| 10 | $Mo_1V_{0.396}Nb_{0.128}Pd_{2.68E-04}$ |
| 11 | $Mo_1V_{0.396}Nb_{0.128}Pd_{2.85E-04}$ |
| 12 | $Mo_1V_{0.396}Nb_{0.128}Pd_{3.84E-04}$ |
| 13 | $Mo_1V_{0.396}Nb_{0.128}Pd_{9.99E-03}$ |
| 14 | $Mo_1V_{0.396}Nb_{0.128}Pd_{1.00E-03}$ |
| 15 | $Mo_1V_{0.396}Nb_{0.128}Pd_{1.50E-03}$ |
| 16 | $Mo_1V_{0.396}Nb_{0.128}Pd_{3.00E-03}$ |
| 17 | $Mo_1V_{0.398}Nb_{0.128}Pd_{3.00E-03}$ |
| 18 | $Mo_1V_{0.396}Nb_{0.128}Pd_{5.00E-03}$ |
| 19 | $Mo_1V_{0.396}Nb_{0.128}Pd_{1.00E-02}$ |

Preparation Procedure for Catalyst Group A

Ammonium metavanadate (Aldrich Chemicals, Assay= 99.0%) in the amount of 11.4 grams was added to 120 ml of distilled water and heated to 90° C. with stirring. 2.5 grams of oxalic acid were added to obtain a clear yellow color solution with a pH between 5 and 6 (Solution A). 19.4 grams of niobium oxalate (21.5% $Nb_2O_5$, Niobium Products Company, USA) were added to 86 ml of water and heated to 65° C. with continuous stirring to give a clear white color solution with a pH of 1 (Solution B). Solution B was combined with Solution A. The resultant solution was heated at 90° C. and 28 grams of oxalic acid was added very slowly with continuous stirring to give Solution C.

Ammonium paramolybdate tetra hydrated (Aldrich Chemicals A.C.S-12054-85-2) in the amount of 43.2 grams was added to 45 ml of water and heated to 60° C. to give a colorless solution with a pH between 6.0 and 6.5 (Solution D). Solution D was combined slowly with Solution C to give dark blue to dark gray color precipitates (Mixture E). The required amount of palladium was added slowly to gel mixture. This dark color combination was stirred vigorously to achieve a homogeneous gel mixture which was then dried slowly to incipient dryness within 60 to 120 minutes at 95–98° C. with continuous stirring.

The resulting solid was put in a China dish and dried additionally in an oven at 120° C. for sixteen hours. The dried material was cooled to room temperature and placed in a furnace. The temperature was raised from room temperature to 350° C. at the rate of 2°/min. and thereafter held at 350° C. for four hours.

Calcined catalyst was formulated into uniform particles of the 40–60 mesh size and evaluated for the ethane oxidative dehydrogenation reaction. Examples 7, 8, and 9 were prepared using the same method to check the reproducibility of the catalytic materials.

Preparation Procedure for Catalyst Group B

Ammonium metavanadate (Aldrich Chemicals, Assay= 99.0%) in the amount of 7.6 grams was added to 80 ml of distilled water and heated to 90° C. with stirring. A yellow color solution with pH between 5 and 6 was obtained (Solution A). 3.4 grams of niobium hydrate oxide (80% $Nb_2O_5$, Niobium Products Company, USA) and 20 grams of oxalic acid were added to 80 ml of water and heated to 95° C. with continuous stirring to give a clear white color solution with a pH of 0.57 (Solution B). Solution A and B were mixed together at 90° C. with continuous stirring of the content of the mixture. Color changes from pale yellow to brown to green to dark green were observed. The pH of the solution was 1.20 at 85° C. 8 g of oxalic acid was added very slowly to the solution with continues stirring of the content of the mixture at 90° C. A dark blue-green color solution with a pH of 0.86 at 86° C. was obtained (Solution C).

Ammonium paramolybdate tetra hydrated (Aldrich Chemicals A.C.S-12054-85-2) in the amount of 28.8 grams was added to 30 ml of water and heated to 60° C. to give a colorless solution with a pH between 5.0 and 6.0 (Solution D). Solution D was combined slowly with Solution C to give dark blue to dark gray color precipitates (Mixture E). The required amount of palladium as Pd-alumina was-added slowly to gel mixture. This dark color combination was stirred vigorously to achieve a homogeneous gel mixture which was then dried slowly to incipient dryness within 60 to 120 minutes at 95–98° C. with continuous stirring.

The resulting solid was put in a China dish and dried additionally in an oven at 120° C. for sixteen hours. The dried material was cooled to room temperature and placed in a furnace. The temperature was raised from room temperature to 350° C. at the rate of 2°/min. and thereafter held at 350° C. for four hours.

Calcined catalyst was formulated into uniform particles of the 40–60 mesh size and evaluated for the ethane oxidative dehydrogenation reaction.

Preparation Procedure for Catalyst Group C

Ammonium metavanadate (Aldrich Chemicals, Assay= 99.0%) in the amount of 3.42 grams was added to 90 ml of distilled water and heated to 87° C. (Solution A). 5.82 grams of niobium oxalate (21.5% $Nb_2O_5$, Niobium Products Company, USA) was added to 25.8 ml of water and heated to 63° C. with continuous stirring to give a turbid white color solution (Solution B). Solution B was combined with Solution A. The resultant solution was heated at 90° C. and 9 grams of oxalic acid was added very slowly with continuous stirring to give Solution C. Ammonium paramolybdate tetra hydrated (Aldrich Chemicals A.C.S 12054-85-2) in the amount of 12.96 grams was added to 13.2 ml of water and heated to 50° C. to give a colorless solution (Solution D). Solution D was combined slowly with Solution C to give dark blue to dark gray color precipitates (Mixture E). The required amount of palladium as Pd charcoal was added slowly to gel mixture. This dark color combination was stirred vigorously to achieve a homogeneous gel mixture which was then dried slowly to incipient dryness.

The resulting solid was put in a China dish and kept at room temperature (25° C.) for one day. Further catalyst was dried in an oven at 120° C. for sixteen hours. The dried material was cooled to room temperature and placed in a furnace. The temperature was raised from room temperature to 350° C. at the rate of 1° C./min. and thereafter held at 350° C. for five hours.

The BET surface area of the catalysts mentioned in the examples (1–19) varies from 25 to 35 $m^2/g$.

Two types of feed systems for catalytic evaluation were applied in order to see the impact of catalyst composition on the product selectivity and activity.

1) Ethane-oxygen (Ethane enriched)
2) Ethane-Air (Ethane leaned).

The results of the tests with these catalysts under the reaction conditions described above are given in Tables 3 and 4.

TABLE 3

Catalyst Evaluation Data for Ethane-Air System
(Reaction condition: 260° C., 200 Psi, Ethane:Air (15%:85%), F/W 10/min.)

| Exam- | Conversion (%) | | Selectivity (%) | | | | Yield (%) |
|---|---|---|---|---|---|---|---|
| ple | Ethane | oxygen | Acetic acid | CO | CO2 | Ethylene | Acetic Acid |
| 1 | 64.69 | 100 | 30.47 | 22.65 | 16.08 | 26.96 | 19.79 |
| 2 | 49.08 | 100 | 47.75 | 0 | 44.8 | 7.49 | 23.44 |
| 3 | 48 | 100 | 49.69 | 0 | 47.42 | 3.31 | 23.85 |
| 4 | 46.76 | 100 | 51.52 | 0 | 49.3 | 0 | 24.09 |
| 5 | 51.03 | 99.3 | 48.22 | 0 | 51.27 | 0.88 | 24.61 |
| 6 | 47.17 | 100 | 52.3 | 0 | 48.56 | 0 | 24.67 |
| 7 | 49.96 | 100 | 54.29 | 0 | 43.88 | 2.34 | 27.12 |
| 8 | 49.7 | 100 | 53.06 | 0 | 43.61 | 3.85 | 26.37 |
| 9 | 47.97 | 100 | 55.07 | 0 | 45.51 | 0 | 26.42 |
| 10 | 49.19 | 100 | 55.74 | o | 42.71 | 1.87 | 27.42 |
| 11 | 49.61 | 100 | 60.27 | 0 | 38.51 | 0.55 | 29.9 |
| 12 | 49.96 | 100 | 53.02 | 0 | 47.86 | 0 | 24.9 |
| 13 | 44.32 | 85.57 | 55.75 | 1.8 | 43.69 | 0.58 | 24.7 |
| 14 | 50.05 | 100 | 48.68 | 0.32 | 47.61 | 4.07 | 24.3 |
| 15 | 48.79 | 100 | 48.21 | 0 | 51.3 | 2.22 | 23.5 |
| 16 | 44.03 | 93.55 | 45.99 | 0 | 56.21 | 0.7 | 20.2 |
| 17 | 47.02 | 100 | 42.61 | 0 | 54.49 | 3.55 | 20.0 |
| 18 | 46.9 | 100 | 37.42 | 0 | 57.3 | 5.94 | 17.5 |
| 19 | 47.3 | 100 | 48.73 | 0 | 49.52 | 2.08 | 23.0 |

TABLE 4

Catalyst Evaluation Data for Ethane-Oxygen System
(Reaction condition: 260° C., 200 Psi, Ethane:Oxygen (82%:18%), F/W = 10/min.)

| Exam- | Conversion (%) | | Selectivity (%) | | | | Yield (%) |
|---|---|---|---|---|---|---|---|
| ple | Ethane | oxygen | Acetic acid | CO | CO2 | Ethylene | Acetic Acid |
| 1 | 12.96 | 47.75 | 22.46 | 4.03 | 2.80 | 26.96 | 2.91 |
| 6 | 8.71 | 57.26 | 59.47 | 1.25 | 12.82 | 28.81 | 5.18 |
| 12 | 9.36 | 60.86 | 63.91 | 0.76 | 14.43 | 20.63 | 5.98 |
| 14 | 10.08 | 70.66 | 57.54 | 0.52 | 15.97 | 26.30 | 5.80 |
| 17 | 11.31 | 77.48 | 67.05 | 0.4 | 16.19 | 15.72 | 7.59 |
| 18 | 11.51 | 82.13 | 65.1 | 0.2 | 16.79 | 15.98 | 7.49 |
| 19 | 9.62 | 79.16 | 73.71 | 0.24 | 21.52 | 6.03 | 7.09 |
| 1** | 20.7 | 97.67 | 31.25 | 6.15 | 4.32 | 60.03 | 6.47 |
| 12** | 13.6 | 100 | 57.23 | 0.47 | 19.24 | 22.27 | 7.78 |
| 19** | 13.57 | 100 | 66.84 | 0 | 25.08 | 10.45 | 9.07 |

**Reaction temperature for these tests is 275° C.

The activities of all the samples were measured using the same amount of catalyst (3 g). The differences in ethane conversion might be caused by the different specific surface areas of catalysts. In this case, catalyst activity can be expressed as the conversion per unit area, Table 5. Evaluation data shows that catalyst without palladium (Example No 1) has a higher specific conversion or activity as compared to Pd family catalysts (Pd containing catalyst). Further, activity in terms of conversion does not change significantly for the palladium family catalysts regardless of varying amount of palladium in the catalysts. This means that addition of palladium to MoNbV metal oxide decreases the specific overall activity. However, this change in the activity is not dependent on the amount of palladium.

TABLE 5

Activity of Catalysts

| Example | BET surace area (m2/g) | Ethane Conversion (%) -E-Air system | Specific conversions (%/m2) |
|---|---|---|---|
| 1 | 25.6 | 64.69 | 0.8423 |
| 2 | 23.00 | 48.00 | 0.6956 |
| 4 | 27.5 | 46.76 | 0.5663 |
| 6 | 29.97 | 47.17 | 0.5246 |
| 7 | 26.08 | 49.96 | 0.6380 |
| 10 | 28.03 | 49.19 | 0.5780 |
| 11 | 29.00 | 49.61 | 0.5663 |
| 12 | 28.81 | 49.96 | 0.5780 |

*S. Conv is Specific conversion of ethane per unit area = Conversion/specific surface area (%/m2)

Palladium-containing mixed oxide catalysts for ethane-air and ethane-oxygen system follows the same selectivity and activity trend, Tables 3 and 4. Total conversion of ethane decreases with the increase in the selectivity of acetic acid. Selectivity to acetic acid passes through a maximum with an increase in the amount of palladium in the mixed oxide catalysts. Further, the amount of ethylene and carbon monoxide (primary reaction products) are completely converted to acetic acid and carbon dioxide, depending on the composition of the catalyst.

It is seen that with the addition of Pd to the MoVNb oxide the following overall changes in catalyst performance are observed:

1. Rate of oxygenation of ethylene to acetic acid increases and passes through maximum with the amount of palladium.
2. Rate of CO oxidation to $CO_2$ increases. Consequently, a decrease in CO selectivity is observed.

The MoVNbPd mixed metal oxide catalysts are redox type catalysts having an ability to be reduced and reoxidized. Over such type of catalysts, dehydrogenation of alkane is a dominant primary reaction producing dehydrogenated products, alkenes and water at short reaction contact times (low hydrocarbon conversion). However, at relatively high contact times and conversions, oxygenated and degradation products are formed from the secondary reactions producing acids and carbon oxides. At high contact time there is a competition of total oxidation reactions leading to CO and $CO_2$ and oxygenation reactions leading to acids.

Selectivity behavior to desired mild oxidation products depends on the types of active centers in the catalysts in addition to other physical reaction parameters, such as hydrocarbon to oxygen ratio, pressure, temperature and contact time. Further, the interaction of surface intermediate with active sites demonstrates the selectivity patterns in oxidation catalysts. Mixed metal oxide phases of MoV are known to be responsible for the oxidative dehydrogenation of ethane, alkane, to ethylene. It has been reported that addition of Nb to MoV oxide improves the selectivity to acetic acid (E. M. Thorsteinson et. al.). Further palladium is known as a total oxidation metal as well as helping to facilitate the oxygenation of alkene. The presently disclosed results for MoVNbPd catalysts demonstrate that there is balance between the oxygenation and total oxidation reaction and this depends on the number or amount of palladium in the mixed oxide catalyst. At low concentrations-of palladium, when Pd atoms are well dispersed at the surfaces, the oxygenation reaction is favored resulting in high selectivity to acetic acid. While at higher concentrations of palladium and the formation of metal crystallites is very possible, total oxidation reaction resulting in higher selectivity to $CO_2$ is favored. Consequently, decreased in acetic acid selectivity at high concentrations of Pd in the catalyst is accounted for. Further, catalytic data also demonstrate that the specific overall catalytic activity of MoVNbPd catalysts having varying amount of palladium does not change considerably but the selectivity to acetic acid increases essentially.

The above description of the invention is intended to be illustrative and not limiting. Various changes or modifications in the embodiments described may occur to those skilled in the art. These can be made without departing from the spirit or scope of the invention.

What is claimed is:

1. A single stage catalytic process for direct conversion of ethane to acetic acid by means of ethane oxidation comprising the step of oxidizing ethane in a reaction mixture comprising ethane and oxygen or a compound capable of providing oxygen in a reaction zone in the presence of a catalyst composition represented by the formula:

$Mo_a V_b Nb_c Pd_d O_x$, where a is 1 to 5;
b is 0 to 0.5;
c is 0.01 to 0.5; and
d is 0 to 0.2;
wherein x is a number determined by the valence requirements of the other elements in the catalyst composition.

2. The process of claim 1, wherein said catalyst is in the form of a fixed or fluidized bed and said oxidation is carried out by a feed mixture comprising ethane introduced into the reaction zone.

3. The process of claim 2, wherein said feed mixture further comprises air.

4. The process of claim 2, wherein said feed mixture comprises oxygen.

5. The process of claim 2, wherein said feed mixture comprises molecular oxygen ranging from 0.1 to 50% by volume of the feed.

6. The process of claim 2, wherein said feed mixture is diluted with steam in an amount ranging from 0 to 40% by volume.

7. The process of claim 1, wherein oxidation is achieved while operating in gas phase at a temperature of from 150 to 450° C., under a pressure of from 1 to 50 bars, and with a contact time between reaction mixture and the catalyst of from 0.1 to 10 seconds.

8. The process of claim 1, wherein said oxidation provides a selectivity to acetic acid of 60% at a 50% conversion of ethane per single pass through said reaction zone.

9. A single stage catalytic process for direct conversion of ethane to acetic acid by means of ethane oxidation comprising the step of oxidizing ethane in a reaction mixture feed comprising ethane and oxygen or a compound capable of providing oxygen in a reaction zone in the presence of a catalyst composition represented by the formula:

$Mo_a V_b Nb_c Pd_d O_x$, where a is 1 to 5;
b is 0 to 0.5;
c is 0.01 to 0.5; and
d is 0 to 0.2;
wherein x is a number determined by the valence requirements of the other elements in the catalyst composition and said oxidation of ethane does not produce CO and ethylene as by-products using molecular oxygen within a range from 0.1 to 50% of the feed.

10. The process of claim 1, further comprising the step of introducing oxygen into the feed mixture to increase the yield, selectivity or both yield and selectivity of acetic acid.

11. The process of claim 1, further comprising the step of introducing oxygen into the reaction zone to increase the yield, selectivity or both yield and selectivity of acetic acid.

12. A process for performing a catalytic chemical reaction in fluid phase comprising at least one reactant in fluid phase under suitable reaction conditions with a catalyst containing a catalyst composition comprising the elements Mo, V, Nb, and Pd in the form of oxides, in the ratio $Mo_a V_b Nb_c Pd_d$ a is 1 to 5;
b is 0 to 0.5
c is 0.01 to 0.5; and
d is 0 to 0.2.

13. A process for performing a catalytic chemical reaction comprising the step of introducing a reactant in fluid phase into a reaction zone containing a catalyst composition having a catalyst composition comprising the elements Mo, V, Nb, and Pd in the form of oxides, in the ratio $Mo_a V_b Nb_c Pd_d$ a is 1 to 5;
b is 0 to 0.5
c is 0.01 to 0.5; and
d is 0 to 0.2.

14. The process of claim 12, wherein said catalytic chemical reaction converts one or more fluid phase reactants to one or more fluid phase products.

15. The process of claim 12, wherein said catalytic chemical reaction oxidizes lower alkenes to corresponding acids.

16. The process of claim 14, wherein said one or more fluid phase reactants comprise ethane and said one or more fluid phase product comprise acetic acid.

17. The process of claim 15, wherein said one or more fluid phase reactants comprise ethane and said one or more fluid phase products comprise acetic acid.

18. The process of claim 14, wherein said one or more fluid phase reactants comprise alpha-beta unsaturated aliphatic aldehydes and oxygen and said one or more fluid phase products comprise alpha-beta unsaturated carboxylic acids.

19. A single stage catalytic process for direct conversion of ethane to acetic acid by means of ethane oxidation comprising the step of oxidizing ethane in a reaction mixture comprising ethane and oxygen or a compound capable of providing oxygen in a reaction zone in the presence of a catalyst made by a process comprising the steps of:

(a) combining the elements Mo, V, Nb and Pd in the following ratio to form a composition having the formula:

$Mo_a V_b Nb_c Pd_d$ a is 1 to 5;
b is 0 to 0.5;
c is 0.01 to 0.5; and
d is 0 to 0.2; and (b) calcining said composition to form said catalyst.

20. The single stage catalytic process of claim 19, wherein d ranges from 4.99E-05 to 5.00E-03.

21. A single stage catalytic process for direct conversion of ethane to acetic acid by means of ethane oxidation comprising the step of oxidizing ethane in a reaction mixture comprising ethane and oxygen or a compound capable of providing oxygen in a reaction zone in the presence of a catalyst composition comprising the elements Mo, V, Nb and Pd in the form of oxides, in the following ratio:
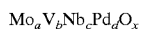
a is 1 to 5;
b is 0 to 0.5;
c is 0.01 to 0.5;
d is 4.99E-05 to 5.00E-03; and
wherein x is a number determined by the valence requirements of the other elements in the catalyst composition.
* * * * *